(12) United States Patent
Lee et al.

(10) Patent No.: US 11,571,726 B2
(45) Date of Patent: Feb. 7, 2023

(54) METHOD FOR DISPOSING OF CONTAMINATED DEPOSIT SOIL AND RECYCLED RECLAMATION SOIL USING SAME

(71) Applicants: Sang-Seob Lee, Seongnam-si (KR); KOREA MARINE ENVIRONMENT MANAGEMENT CORPORATION, Seoul (KR)

(72) Inventors: Sang-Seob Lee, Seongnam-si (KR); Man Jang, Seongnam-si (KR)

(73) Assignees: Sang-Seob Lee, Seongnam-si (KR); KOREA MARINE ENVIRONMENT MANAGEMENT CORPORATION, Seoul (KR)

( * ) Notice: Subject to any disclaimer, the term of this patent is extended or adjusted under 35 U.S.C. 154(b) by 571 days.

(21) Appl. No.: 16/483,883

(22) PCT Filed: Feb. 7, 2018

(86) PCT No.: PCT/KR2018/001630
§ 371 (c)(1),
(2) Date: Oct. 25, 2019

(87) PCT Pub. No.: WO2018/147628
PCT Pub. Date: Aug. 16, 2018

(65) Prior Publication Data
US 2020/0222955 A1 Jul. 16, 2020

(30) Foreign Application Priority Data
Feb. 7, 2017 (KR) .................. 10-2017-0016983

(51) Int. Cl.
*B09C 1/10* (2006.01)
*B09C 1/02* (2006.01)
(Continued)

(52) U.S. Cl.
CPC .................. *B09C 1/10* (2013.01); *B09C 1/02* (2013.01); *B09C 1/08* (2013.01); *C05F 11/08* (2013.01);
(Continued)

(58) Field of Classification Search
None
See application file for complete search history.

(56) References Cited

U.S. PATENT DOCUMENTS 3,616,204 A * 10/1971 Linn .................. B09C 1/10
435/281
4,789,478 A * 12/1988 Revis .................. C02F 3/34
210/611

(Continued)

FOREIGN PATENT DOCUMENTS

KR 20010105915 11/2001
KR 100469480 1/2005
(Continued)

OTHER PUBLICATIONS

International Search Report—PCT/KR2018/001630 dated Jun. 15, 2018.

*Primary Examiner* — Wayne A Langel
(74) *Attorney, Agent, or Firm* — Cantor Colburn LLP

(57) ABSTRACT

Provided is a method for disposing of contaminated deposit soil and recycled reclamation soil using the same and, more specifically, a method for disposing of contaminated dredged soil, the method comprising the steps of: seeding a mixed strain NIX51 (KACC81038BP) in the contaminated dredged soil to primarily dispose of contaminated materials in a bioreactor; and washing the degraded soil, which has been primarily disposed of, with a washing solution containing at least one selected from the group consisting of (Continued)

citric acid, oxalate, carbonic acid ($H_2CO_3$), and nitric acid, to secondarily dispose of heavy metals.

9 Claims, 14 Drawing Sheets

(51) Int. Cl.
    *B09C 1/08*     (2006.01)
    *C05F 11/08*     (2006.01)
    *C09K 17/04*     (2006.01)
    *C09K 17/08*     (2006.01)
    *C09K 17/10*     (2006.01)
    *C12N 1/20*     (2006.01)

(52) U.S. Cl.
    CPC .............. *C09K 17/04* (2013.01); *C09K 17/08* (2013.01); *C09K 17/10* (2013.01); *C12N 1/20* (2013.01)

(56) References Cited

U.S. PATENT DOCUMENTS

| | | | | |
|---|---|---|---|---|
| 5,221,327 A * | 6/1993 | Rusin | ............ | C22B 3/18 75/712 |
| 5,248,329 A * | 9/1993 | Rusin | ............ | C22B 3/18 75/715 |
| 5,427,944 A * | 6/1995 | Lee | ............ | B09C 1/10 435/262.5 |
| 5,494,649 A * | 2/1996 | Fristad | ............ | C22B 25/04 423/27 |
| 5,614,410 A * | 3/1997 | Mueller | ............ | B09C 1/10 435/262.5 |
| 5,658,795 A * | 8/1997 | Kato | ............ | C02F 3/108 435/262.5 |
| 6,204,430 B1 * | 3/2001 | Baldwin | ............ | C09K 17/02 588/2 |
| 6,420,164 B1 * | 7/2002 | Eccles | ............ | B09C 1/10 435/262 |
| 2007/0051676 A1 * | 3/2007 | Chandraghatgi | ......... | B09C 1/10 210/611 |
| 2010/0279387 A1 * | 11/2010 | Fujita | ............ | B09C 1/02 435/252.1 |
| 2014/0042087 A1 * | 2/2014 | O'Driscoll | ............ | B09C 1/06 210/606 |
| 2014/0273150 A1 * | 9/2014 | Angel | ............ | C02F 3/342 435/186 |
| 2017/0008052 A1 * | 1/2017 | Nam | ............ | B09C 1/08 |

FOREIGN PATENT DOCUMENTS

| | | | |
|---|---|---|---|
| KR | 101151608 | 6/2012 | |
| KR | 101287434 | 7/2013 | |
| KR | 101443724 | 9/2014 | |
| KR | 101573624 | 12/2015 | |
| WO | WO 2018/153447 A1 * | 8/2018 | ............. A01N 63/00 |

* cited by examiner

FIG. 1

| | Quality Inspection Report | | | | | | | |
|---|---|---|---|---|---|---|---|---|
| 01.Test Sample (Producing country) Dredged marine soil | | | | 09.Registration Date: August 11, 2016 | | | | |
| 02.Location of control | | | | 10.Test No. 11-1313 | | | | |
| 03.Purpose of use: Review of suitability for reclamation material (for research) | | | | 11.Date: August 5, 2016 | | | | |
| 04.Project - | | | | 12.Sampled by ECM Sangsub Lee | | | | |
| 05.Client - | | | | 13.Observer - | | | | |
| 06.Constructor - | | | | 14.Producer - | | | | |
| 07.Requested by ECM Sangsub Lee | | | | | | | | |
| 08.National Major Facility: Not Applicable | | | | | | | | |
| The quality test requested was performed for the indicated sample. In accordance with Paragraph 3 of Article 56 of the Enforcement Rule of the Construction Technology Promotion Act, we hereby inform you of the test result. | | | | | | | | |
| Test Result | | | | | | | | |
| No. | Test Items | | Test Method | Test Results | | Responsible Engineer | | Tester |
| | | | | | | Qualification and Certificate No. | Name | Signature | Name | Signature |
| 1 | Natural Moisture | | KSF 2306-15 | 110.5 | % | Construction Material Testing Technician 102041704840 | Seo Sanghong | | Lee Jeeseong | |
| 2 | Density | | KSF 2308-06 | 2.600 | g/cm³ | | | | | |
| 3 | Liquid Limit | | KSF 2303-15 | 54.7 | % | | | | | |
| | Plastic Limit | | | 28.3 | % | | | | | |
| | Plastic Index | | | 26.4 | - | | | | | |
| 4 | Particle Size | Max Size | KSF 2302-02 | 0.85 | mm | | | | | |
| | | 5mm Sieve passing | | 100 | % | | | | | |
| 5 | 0.08mm Sieve passing | | KSF 2309-09 | 98.7 | % | | | | | |
| 6 | Classification | | KSF 2324-06 | CH | - | | | | | |
| This test result is only based on the samples submitted for test and inspection. It is prohibited to use the result for other purposes. | | | | | | | | | | |

August 25, 2016

Korea Research Institute For Construction Testing (Construction Engineering Services) President Sungsoo KIM Address: 26, Ugok-ro 217beon-gil, Uichang-gu, Changwon-si, Gyeongsangnam-do, Republic of Korea / Telephone:(055)238-6200/Fax:(055)238-6765

Note
1. "National Major Facility (name of the facility)" should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.
· Note: The result cannot be guaranteed unless the names and signatures of the responsible engineer and tester are indicated.

Management-120-1(Poom)

FIG. 2

Quality Inspection Report

01. Test Sample (Producing country) Dredged marine soil  
02. Location of NO.1  
03. Purpose of use: Review of suitability for reclamation material (for research)  
04. Project -  
05. Client -  
06. Constructor -  
07. Requested by ECM Sangsub Lee  
08. National Major Facility: Not Applicable 09. Registration Date: August 11, 2016  
10. Test No. 11-1313  
11. Date: August 5, 2016  
12. Sampled by ECM Sangsub Lee  
13. Observer -  
14. Producer -

The quality test requested was performed for the indicated sample. In accordance with Paragraph 3 of Article 56 of the Enforcement Rule of the Construction Technology Promotion Act, we hereby inform you of the test result.

Test Result

| No. | Test Items | | Test Method | Test Results | | Responsible Engineer | | | Tester | |
|---|---|---|---|---|---|---|---|---|---|---|
| | | | | | | Qualification and Certificate No. | Name | Signature | Name | Signature |
| 1 | Natural Moisture | | KSF 2306-15 | 50.3 | % | Construction Material Testing Technician 102041704840 | Seo Sangbong | | Lee Jaeseong | |
| 2 | Density | | KSF 2308-06 | 2.677 | g/cm³ | | | | | |
| 3 | Liquid Limit | | KSF 2303-15 | 50.5 | % | | | | | |
| | Plastic Limit | | | 26.7 | % | | | | | |
| | Plastic Index | | | 23.8 | - | | | | | |
| 4 | Particle Size | Max Size | KSF 2302-02 | 4.75 | mm | | | | | |
| | | 5mm Sieve passing | | 100 | % | | | | | |
| 5 | 0.08mm Sieve passing | | KSF 2309-09 | 59.8 | % | | | | | |
| 6 | Classification | | KSF 2324-06 | CH | - | | | | | |

· This test result is only based on the samples submitted for test and inspection. It is prohibited to use the result for other purposes.

August 25, 2016  
Korea Research Institute For Construction Testing (Construction Engineering Services) President Sungsoo KIM  
Address: 26, Ugok-ro 217beon-gil, Uichang-gu, Changwon-si, Gyeongsangnam-do, Republic of Korea / Telephone:(055)238-6200/Fax:(055)238-6765

Note
1. "National Major Facility (name of the facility)" should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.
· Note: The result cannot be guaranteed unless the names and signatures of the responsible engineer and tester are indicated.

Management-120-1(Poom)

FIG. 3

Quality Inspection Report

| | |
|---|---|
| 01. Test Sample (Producing country) Dredged marine soil | 09. Registration Date: August 11, 2016 |
| 02. Location of NO.2 | 10. Test No. 11-1313 |
| 03. Purpose of use: Review of suitability for reclamation material (for research) | 11. Date: August 5, 2016 |
| 04. Project - | 12. Sampled by ECM Sangsub Lee |
| 05. Client - | 13. Observer - |
| 06. Constructor - | 14. Producer - |
| 07. Requested by ECM Sangsub Lee | |
| 08. National Major Facility: Not Applicable | |

The quality test requested was performed for the indicated sample. In accordance with Paragraph 3 of Article 56 of the Enforcement Rule of the Construction Technology Promotion Act, we hereby inform you of the test result.

Test Result

| No. | Test Items | | Test Method | Test Results | | Responsible Engineer | | | Tester | |
|---|---|---|---|---|---|---|---|---|---|---|
| | | | | | | Qualification and Certificate No. | Name | Signature | Name | Signature |
| 1 | Natural Moisture | | KSF 2306-15 | 48.9 | % | Construction Material Testing Technician 102041704840 | Seo Sangbong | | Lee Jaeseong | |
| 2 | Density | | KSF 2308-06 | 2.685 | g/cm³ | | | | | |
| 3 | Liquid Limit | | KSF 2303-15 | 47.9 | % | | | | | |
| | Plastic Limit | | | 25.2 | % | | | | | |
| | Plastic Index | | | 22.7 | - | | | | | |
| 4 | Particle Size | Max Size | KSF 2302-02 | 4.75 | mm | | | | | |
| | | 5mm Sieve passing | | 100 | % | | | | | |
| 5 | 0.08mm Sieve passing | | KSF 2309-09 | 56.9 | % | | | | | |
| 6 | Classification | | KSF 2324-06 | CL | - | | | | | |

- This test result is only based on the samples submitted for test and inspection. It is prohibited to use the result for other purposes.

August 25, 2016

Korea Research Institute For Construction Testing (Construction Engineering Services) President Sungsoo KIM Address: 26, Ugok-ro 217beon-gil, Uichang-gu, Changwon-si, Gyeongsangnam-do, Republic of Korea / Telephone:(055)238-6200/Fax:(055)238-6765

Note
1. "National Major Facility (name of the facility)" should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.
- Note: The result cannot be guaranteed unless the names and signatures of the responsible engineer and tester are indicated.

2/9

Management-120-1(Poom)

FIG. 4

| | Quality Inspection Report | | | | | | |
|---|---|---|---|---|---|---|---|
| 01.Test Sample (Producing country) Dredged marine soil | | | 09.Registration Date: August 11, 2016 | | | | |
| 02.Location of NO.3 | | | 10.Test No. 11-1313 | | | | |
| 03.Purpose of use: Review of suitability for reclamation material (for research) | | | 11.Date: August 5, 2016 | | | | |
| 04.Project – | | | 12.Sampled by ECM Sangsub Lee | | | | |
| 05.Client – | | | 13.Observer – | | | | |
| 06.Constructor – | | | 14.Producer – | | | | |
| 07.Requested by ECM Sangsub Lee | | | | | | | |
| 08.National Major Facility: Not Applicable | | | | | | | |

The quality test requested was performed for the indicated sample. In accordance with Paragraph 3 of Article 56 of the Enforcement Rule of the Construction Technology Promotion Act, we hereby inform you of the test result.

Test Result

| No. | Test Items | | Test Method | Test Results | | Responsible Engineer | | Tester | |
|---|---|---|---|---|---|---|---|---|---|
| | | | | | | Qualification and Certificate No. | Name Signature | Name | Signature |
| 1 | Natural Moisture | | KSF 2306-15 | 64.4 | % | Construction Material Testing Technician 102041704840 | Seo Sangbong | Lee Jaeseong | |
| 2 | Density | | KSF 2308-06 | 2.658 | g/cm³ | | | | |
| 3 | Liquid Limit | | KSF 2303-15 | 57.8 | % | | | | |
| | Plastic Limit | | | 27.2 | % | | | | |
| | Plastic Index | | | 30.6 | – | | | | |
| 4 | Particle Size | Max Size | KSF 2302-02 | 9.5 | mm | | | | |
| | | 5mm Sieve passing | | 78 | % | | | | |
| 5 | 0.08mm Sieve passing | | KSF 2309-09 | 57.5 | % | | | | |
| 6 | Classification | | KSF 2324-06 | CH | – | | | | |

· This test result is only based on the samples submitted for test and inspection. It is prohibited to use the result for other purposes.

August 25, 2016

Korea Research Institute For Construction Testing  (Construction Engineering Services)  President Sungsoo KIM Address: 26, Ugok-ro 217beon-gil, Uichang-gu, Changwon-si, Gyeongsangnam-do, Republic of Korea / Telephone:(055)238-6200/Fax:(055)238-6765

Note
1. "National Major Facility (name of the facility)" should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.

· Note: The result cannot be guaranteed unless the names and signatures of the responsible engineer and tester are indicated.

3/9

Management-120-1(Poom)

FIG. 5

Quality Inspection Report

01. Test Sample (Producing country) Dredged marine soil
02. Location of NO.4
03. Purpose of use: Review of suitability for reclamation material (for research)
04. Project -
05. Client -
06. Constructor -
07. Requested by ECM Sangsub Lee
08. National Major Facility: Not Applicable 09. Registration Date: August 11, 2016
10. Test No. 11-1313
11. Date: August 5, 2016
12. Sampled by ECM Sangsub Lee
13. Observer -
14. Producer -

The quality test requested was performed for the indicated sample. In accordance with Paragraph 3 of Article 56 of the Enforcement Rule of the Construction Technology Promotion Act, we hereby inform you of the test result.

Test Result

| No. | Test Items | | Test Method | Test Results | | Responsible Engineer | | | Tester | |
|---|---|---|---|---|---|---|---|---|---|---|
| | | | | | | Qualification and Certificate No. | Name | Signature | Name | Signature |
| 1 | Natural Moisture | | KSF 2306-15 | 60.1 | % | Construction Material Testing Technician 102041704840 | Seo Sangbong | | Lee Jaeseong | |
| 2 | Density | | KSF 2308-06 | 2.653 | g/cm³ | | | | | |
| 3 | Liquid Limit | | KSF 2303-15 | 56.8 | % | | | | | |
| | Plastic Limit | | | 27.6 | % | | | | | |
| | Plastic Index | | | 29.2 | - | | | | | |
| 4 | Particle Size | Max Size | KSF 2302-02 | 9.5 | mm | | | | | |
| | | 5mm Sieve passing | | 82 | % | | | | | |
| 5 | 0.08mm Sieve passing | | KSF 2309-09 | 66.1 | % | | | | | |
| 6 | Classification | | KSF 2324-06 | CH | - | | | | | |

· This test result is only based on the samples submitted for test and inspection. It is prohibited to use the result for other purposes.

August 25, 2016

Korea Research Institute For Construction Testing (Construction Engineering Services) President Sungsoo KIM Address: 26, Ugok-ro 217beon-gil, Uichang-gu, Changwon-si, Gyeongsangnam-do, Republic of Korea / Telephone:(055)238-6200/ Fax:(055)238-6765

Note
1. "National Major Facility (name of the facility)" should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.
· Note: The result cannot be guaranteed unless the names and signatures of the responsible engineer and tester are indicated.

Management-120-1(Poom)

FIG. 6

Quality Inspection Report

01. Test Sample (Producing country) Dredged marine soil
02. Location of NO.7
03. Purpose of use: Review of suitability for reclamation material (for research)
04. Project –
05. Client –
06. Constructor –
07. Requested by ECM Sangsub Lee
08. National Major Facility: Not Applicable 09. Registration Date: August 11, 2016
10. Test No. 11-1313
11. Date: August 5, 2016
12. Sampled by ECM Sangsub Lee
13. Observer –
14. Producer –

The quality test requested was performed for the indicated sample. In accordance with Paragraph 3 of Article 56 of the Enforcement Rule of the Construction Technology Promotion Act, we hereby inform you of the test result.

Test Result

| No. | Test Items | | Test Method | Test Results | | Responsible Engineer | | | Tester | |
|---|---|---|---|---|---|---|---|---|---|---|
| | | | | | | Qualification and Certificate No. | Name | Signature | Name | Signature |
| 1 | Natural Moisture | | KSF 2306-15 | 68.0 | % | Construction Material Testing Technician 102041704840 | Seo Sangbong | | Lee Jaeseong | |
| 2 | Density | | KSF 2308-06 | 2.656 | g/cm³ | | | | | |
| 3 | | Liquid Limit | KSF 2303-15 | 57.5 | % | | | | | |
| | | Plastic Limit | | 25.9 | % | | | | | |
| | | Plastic Index | | 31.6 | – | | | | | |
| 4 | Particle Size | Max Size | KSF 2302-02 | 4.75 | mm | | | | | |
| | | 5mm Sieve passing | | 100 | % | | | | | |
| 5 | 0.08mm Sieve passing | | KSF 2309-09 | 93.5 | % | | | | | |
| 6 | Classification | | KSF 2324-06 | CH | – | | | | | |

· This test result is only based on the samples submitted for test and inspection. It is prohibited to use the result for other purposes.

August 25, 2016
Korea Research Institute For Construction Testing (Construction Engineering Services) President Sungsoo KIM
Address: 26, Ugok-ro 217beon-gil, Uichang-gu, Changwon-si, Gyeongsangnam-do, Republic of Korea / Telephone:(055)238-6200/Fax:(055)238-6765

Note
1. "National Major Facility (name of the facility)," should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.
· Note: The result cannot be guaranteed unless the names and signatures of the responsible engineer and tester are indicated.

7/9

Management-120-1(Poom)

FIG. 7

Quality Inspection Report

01. Test Sample (Producing country) Dredged marine soil
02. Location of NO.8
03. Purpose of use: Review of suitability for reclamation material (for research)
04. Project –
05. Client –
06. Constructor –
07. Requested by ECM Sangsub Lee
08. National Major Facility: Not Applicable 09. Registration Date: August 11, 2016
10. Test No. 11-1313
11. Date: August 5, 2016
12. Sampled by ECM Sangsub Lee
13. Observer –
14. Producer –

The quality test requested was performed for the indicated sample. In accordance with Paragraph 3 of Article 56 of the Enforcement Rule of the Construction Technology Promotion Act, we hereby inform you of the test result.

Test Result

| No. | Test Items | | Test Method | Test Results | | Responsible Engineer | | | Tester | |
|---|---|---|---|---|---|---|---|---|---|---|
| | | | | | | Qualification and Certificate No. | Name | Signature | Name | Signature |
| 1 | Natural Moisture | | KSF 2306-15 | 70.9 | % | Construction Material Testing Technician 102041704840 | Seo Sangbong | | Lee Jaeseong | |
| 2 | Density | | KSF 2308-06 | 2.653 | g/cm³ | | | | | |
| 3 | Liquid Limit | | KSF 2303-15 | 55.1 | % | | | | | |
| | Plastic Limit | | | 26.9 | % | | | | | |
| | Plastic Index | | | 28.2 | – | | | | | |
| 4 | Particle Size | Max Size | KSF 2302-02 | 4.75 | mm | | | | | |
| | | 5mm Sieve passing | | 100 | % | | | | | |
| 5 | 0.08mm Sieve passing | | KSF 2309-09 | 94.8 | % | | | | | |
| 6 | Classification | | KSF 2324-06 | CH | – | | | | | |

· This test result is only based on the samples submitted for test and inspection. It is prohibited to use the result for other purposes.

August 25, 2016

Korea Research Institute For Construction Testing (Construction Engineering Services)   President Sungsoo KIM Address: 26, Ugok-ro 217beon-gil, Uichang-gu, Changwon-si, Gyeongsangnam-do, Republic of Korea / Telephone: (055)238-6200 / Fax: (055)238-6765

Note
1. "National Major Facility (name of the facility)" should be indicated for National Major Facility.
2. The National Major Facility refers to the Presidential Office, the National Assembly, the Supreme Court, the National Intelligence Service, the central government building, the nuclear power plant, a power plant with a capacity of 1 million kW or more, public radio stations broadcasted nationwide, TV stations, transmission facilities with radio broadcasting transmission power of 5 million kW or more, military facilities, airports and dams.

· Note: The result cannot be guaranteed unless the names and signatures of the responsible engineer and tester are indicated.

8/9

Management-120-1(Poom)

FIG. 9

| KOREA RESEARCH INSTITUTE FOR CONSTRUCTION TESTING ||||
|---|---|---|---|
| TEST DATA SHEET FOR SOIL PROPERTYS ||||
| 01. Category № 2-1608-11 || 07. Sampled by LEE, Sang-Seob ||
| 02. Test № 11-1313 || 08. Observer — ||
| 03. Description Marine dredged soil || 09. Project — ||
| 04. Location NO.1 || 10. Client — ||
| 05. Sampled Date 2016-08-05 || 11. Constructor — ||
| 06. Tested Date 2016-08-11~25 || 12. Requested by LEE, Sang-Seob ||
| TEST RESULT ||||
| 01. Density (KS F2308) 2.677 g/cm³ | 06. Max Size 4.75 mm || 11. Curvature 0.4 |
| 02. Natural Moisture (KS F2306) 50.3 % | 07. 60 % Size 0.077 mm || 12. 5mm Sieve Passing 100 % |
| 03. Liquid Limit (KS F2303) 50.5 % | 08. 30 % Size 0.0089 mm || 13. 2mm Sieve Passing 94 % |
| 04. Plastic limit (KS F2303) 26.7 % | 09. 10 % Size 0.0024 mm || 14. 0.08㎜ Sieve Passing (KS F2309) 59.8 % |
| 05. Plastic Index 23.8 | 10. Uniformity 32 || 15. Classification CH |
| Grain Size Accumulation Curve (KS F2302) ||||
| Gravel | Sand | Silt | Clay | Colloids |
| Greater than or equal to 2.0 mm | 0.074 mm to 2.0 mm | 0.005 mm to 0.074 mm | 0.001 mm to 0.005 mm | Less than or equal to 0.001 mm |

August 25, 2016

1/9

Management-081-1(Poom)

FIG. 11

| KOREA RESEARCH INSTITUTE FOR CONSTRUCTION TESTING ||||
|---|---|---|---|
| TEST DATA SHEET FOR SOIL PROPERTYS ||||
| 01. Category № | 2-1608-11 | 07. Sampled by | LEE, Sang-Seob |
| 02. Test № | 11-1313 | 08. Observer | — |
| 03. Description | Marine dredged soil | 09. Project | — |
| 04. Location | NO.3 | 10. Client | — |
| 05. Sampled Date | 2016-08-05 | 11. Constructor | — |
| 06. Tested Date | 2016-08-11~25 | 12. Requested by | LEE, Sang-Seob |

| TEST RESULT ||||||
|---|---|---|---|---|---|
| 01. Density (KS F2308) | 2.658 g/cm³ | 06. Max Size | 9.5 mm | 11. Curvature | 1.8 |
| 02. Natural Moisture (KS F2306) | 64.4 % | 07. 60 % Size | 0.088 mm | 12. 5mm Sieve Passing | 78 % |
| 03. Liquid Limit (KS F2303) | 57.8 % | 08. 30 % Size | 0.033 mm | 13. 2mm Sieve Passing | 67 % |
| 04. Plastic limit (KS F2303) | 27.2 % | 09. 10 % Size | 0.007 mm | 14. 0.08mm Sieve Passing (KS F2309) | 57.5 % |
| 05. Plastic Index | 30.6 | 10. Uniformity | 13 | 15. Classification | CH |

Grain Size Accumulation Curve (KS F2302)

| Gravel | Sand | Silt | Clay | Colloids |
|---|---|---|---|---|
| Greater than or equal to 2.0 mm | 0.074 mm to 2.0 mm | 0.005 mm to 0.074 mm | 0.001 mm to 0.005 mm | Less than or equal to 0.001 mm |

August 25, 2016

3/9

Management-081-1(Poom)

FIG. 14

| KOREA RESEARCH INSTITUTE FOR CONSTRUCTION TESTING |||||
|---|---|---|---|---|
| TEST DATA SHEET FOR SOIL PROPERTYS |||||
| 01. Category № | 2-1608-11 || 07. Sampled by | LEE, Sang-Seob |
| 02. Test № | 11-1313 || 08. Observer | – |
| 03. Description | Marine dredged soil || 09. Project | – |
| 04. Location | NO.8 || 10. Client | – |
| 05. Sampled Date | 2016-08-05 || 11. Constructor | – |
| 06. Tested Date | 2016-08-11~25 || 12. Requested by | LEE, Sang-Seob |
| TEST RESULT |||||
| 01. Density (KS F2308) 2.653 g/cm³ || 06. Max Size 4.75 mm || 11. Curvature 0.4 |
| 02. Natural Moisture (KS F2306) 70.9 % || 07. 60 % Size 0.045 mm || 12. 5mm Sieve Passing 100 % |
| 03. Liquid Limit (KS F2303) 55.1 % || 08. 30 % Size 0.008 mm || 13. 2mm Sieve Passing 99 % |
| 04. Plastic limit (KS F2303) 26.9 % || 09. 10 % Size 0.0032 mm || 14. 0.08mm Sieve Passing (KS F2309) 94.8 % |
| 05. Plastic Index 28.2 || 10. Uniformity 14 || 15. Classification CH |
| Grain Size Accumulation Curve (KS F2302) |||||
| Gravel | Sand | Silt | Clay | Colloids |
| Greater than or equal to 2.0 mm | 0.074 mm to 2.0 mm | 0.005 mm to 0.074 mm | 0.001 mm to 0.005 mm | Less than or equal to 0.001 mm |

August 25, 2016

METHOD FOR DISPOSING OF CONTAMINATED DEPOSIT SOIL AND RECYCLED RECLAMATION SOIL USING SAME

TECHNICAL FIELD

The present disclosure relates to a method for treating contaminated deposit soil and reclamation technology, and more specifically, relates to a method for treating marine and terrestrial deposit soil multi-contaminated by a high concentration of organic or inorganic materials and a reclamation method using the same.

Background Art

Dredged sand generated by port development and operations in Korea is mostly disposed in landfills formed on the coast, and a portion thereof is disposed of in the ocean. A recycling rate thereof is merely about 10%. Currently, dredging sites are close to saturation. Due to environmental problems, construction of dredged soil disposal sites is difficult in reality.

In particular, as standards and procedures for ocean disposal are strict, it is preferable that recyclability be first considered when dredged materials can be used for engineering, agricultural and environmental improvements, or the like. However, uses and standards related to the recycling of dredged materials are explicitly indicated in legal regulations, and it is difficult to meet the standard of ocean disposal with highly contaminated dredged materials. Further, the ocean disposal of dredged materials involves high disposal and delivery costs. Accordingly, there is an urgent need for dredged soil treatments to develop uses for contaminant purification and recycling.

There has been no application of treatment technology in Korea to reduce a contamination degree, due to a fact that the ocean disposal standards were not applied to dredged soil collected prior to 2008. Particle separation and washing methods are applied at some contaminated deposit purification sites.

Meanwhile, an optimal use for recycling a large amount of dredged marine soil is as an aggregate in precast concrete, corresponding to an amount of the dredged marine soil. The recycling of the dredged soil as aggregate involves removal of contaminants of the dredged soil, and in consideration of washing and screening processes, the recycling process is simple and the economics thereof can be secured. The global construction aggregate market is growing at an annual rate of 5.2%, and the market for secondary concrete products in Korea is steadily growing larger. Accordingly, demand for aggregate is expected to increase.

Accordingly, when a method for effectively treating contaminated dredged soil is provided, it is expected that the method will be widely used in related fields, such as a field of concretes.

(Patent Document 1) Korean Patent Application No. 10-2014-0100214

DISCLOSURE

Technical Problem

An aspect of the present disclosure is to provide a method for effectively treating contaminated deposit soil.

Another aspect of the present disclosure is to provide reclamation soil recycled from contaminated deposit soil purified by the present disclosure.

Technical Solution

According to an aspect of the present disclosure, a method for treating contaminated dredged soil, including inoculating a mixed strain NIX51 (KACC81038BP) in the contaminated deposit soil to treat an organic contaminated material in a bioreactor (a first treatment) and washing the treated deposit soil with a washing solution comprising at least one selected from the group consisting of citric acid, oxalate, carbonic acid $H_2CO_3$) and nitric acid to dispose of a heavy metal (a second treatment) is provided.

According to another aspect of the present disclosure, reclamation soil including deposit soil treated according to the present disclosure is provided.

Advantageous Effects

According to the present disclosure, the contamination of deposit soil, which is mostly treated to be discharged offshore, can be reduced by simple and economical processes, and such purified deposit soil may be recycled as a construction material.

DESCRIPTION OF DRAWINGS

FIGS. 1 to 7 show results of test analysis of bricks prepared to have the compositions of Table 11, performed by the Korea Research Institute for Construction Testing.

FIGS. 8 to 14 show results of evaluations of suitability of the compositions of Table 11 as reclamation soil, performed by the Korea Research Institute for Construction Testing.

BEST MODE FOR INVENTION

Figure 8:
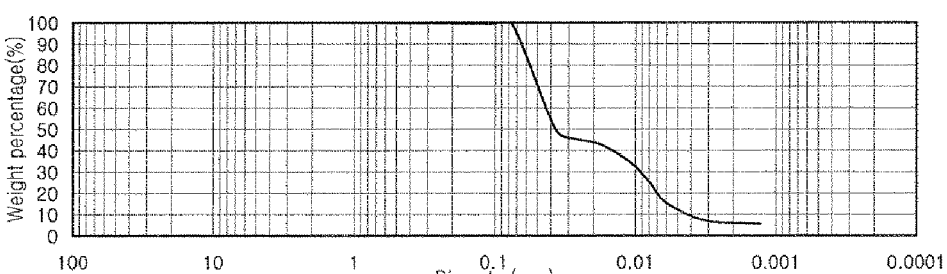
Figure 10:
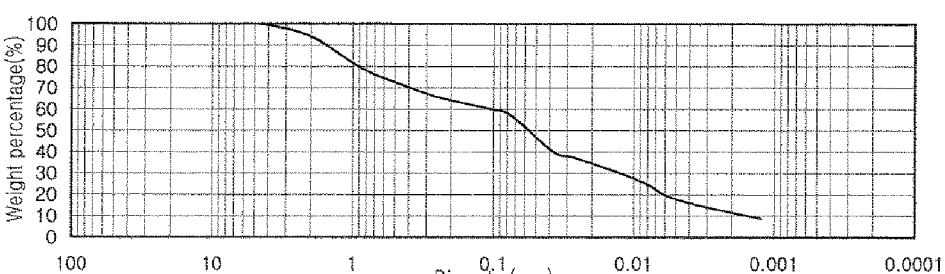
Figure 12:
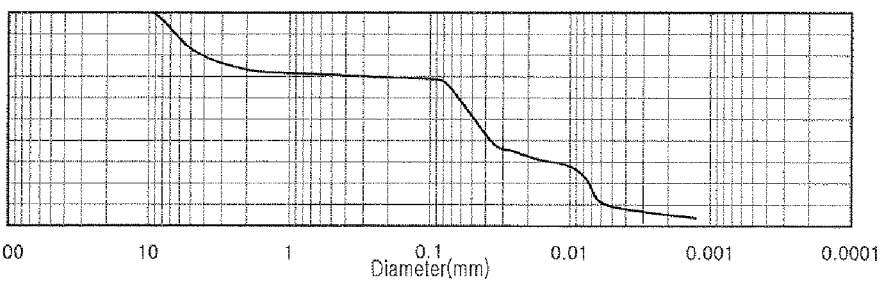
Figure 13:
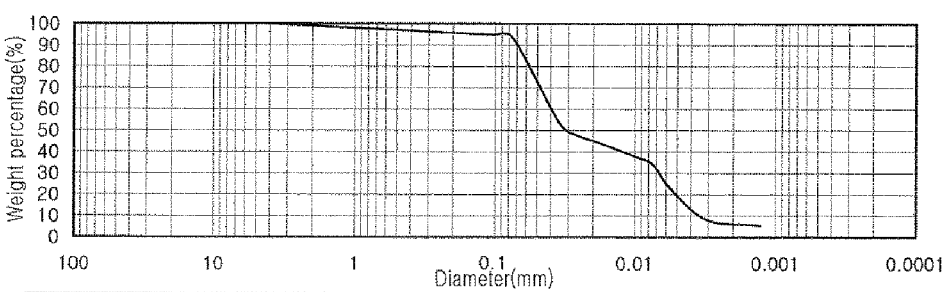

Hereinafter, exemplary embodiments of the present disclosure will be described as follows with reference to the attached drawings. The present disclosure may, however, be embodied in many different forms and should not be construed as being limited to the exemplary embodiments set forth herein.

According to the present disclosure, provided are a method for treating multi-contaminated deposit soil and a recycling method using the same.

More specifically, the method of the present disclosure for treating contaminated dredged soil includes a first treatment involving inoculating a mixed strain NIX51 (KACC81038BP) in the contaminated deposit soil to treat an organic contaminated material in a bioreactor, and a second treatment involving washing the treated deposit soil with a washing solution comprising at least one selected from the group consisting of citric acid, oxalate, carbonic acid ($H_2CO_3$) and nitric acid to treat with a heavy metal.

The mixed strain NIX51 (KACC81038BP), which can be used in the present disclosure, was deposited in the National Institute of Agricultural Sciences Korean Agricultural Culture Collection (KACC) under Accession No. KACC81038BP on Dec. 22, 2016.

Contaminated deposit soil, which can be treated by the present disclosure, includes both marine deposit soil and terrestrial deposit soil, and may be at least one multi-contamination selected from the group consisting of oil (benzene, toluene, ethylbenzene, xylene; BTEX), total petroleum hydrocarbons (TPH), polycyclic aromatic hydrocarbon (PAH), nutrient salts and trichloroethylene (TCE).

More specifically, the contaminants of the contaminated deposit soil may include multi-contamination selected from the group consisting of oils including benzene, toluene, ethylbenzene and xylene, TPH including diesel or the like, PAT including phenanthrene, anthracene, benzo[a]pyrene or the like, nutritive salts including nitrogen, phosphorous or the like, and TCE.

According to the contaminated deposit soil treatment method of the present disclosure, such multi-contamination can be effectively removed. The second treatment is performed after the first treatment in order to remove heavy metals.

For the first treatment, the mixed strain is inoculated in an amount of 0.1 g to 2 g by wet weight per 1 Kg of the deposit soil, preferably 0.5 g to 1.0 g, more preferably 0.1 g to 0.5 g, and for example, in an amount of $1 \times 10^{10}$ per 1 Kg of the dredged soil. When the amount of the mixed strain is less than 0.1 g by wet weight per 1 Kg of the dredged soil, purification efficiency of contaminants by the mixed strain may decrease, leading to a longer time required to treat the contaminants. When the amount of the mixed strain is greater than 2 g, treatment efficiency does not significantly increase compared to an increased amount of the strain, thereby giving rise to an economical issue of increased germiculture material costs. However, the amount of the inoculated strain is not limited thereto, and may vary according to types and concentrations of the contaminant and contaminated deposit soil conditions.

Meanwhile, it is preferable that the first treatment be carried out at 10° C. to 35° C. at pH 6.5 to pH 7.5 under aerobic conditions for 3 days to 14 days.

A temperature of the first treatment is 10° C. to 35° C., preferably 20° C. to 25° C., more preferably 25° C. When the temperature is below 10° C. or above 35° C., activity of the mixed strain is reduced, thereby increasing a treatment time thereof.

A pH of the first treatment is 5.5 to 8.0, preferably 6.8 to 7. When the pH is below 5.5 or above 8.0, organic contaminant purification efficiency decreases, thereby increasing a treatment time thereof.

The first treatment is performed for 3 days to 14 days, preferably 3 days to 7 days. The first treatment may be completed in 3 days according to the types and concentrations of the contaminants, and may last longer in the case of a high TPH concentration of 20,000 or higher. A treatment period varies depending on the contaminant types and concentrations of contaminated deposit soil, and thus is not limited thereto.

According to the method of the present disclosure for treating contaminated deposit soil, such multi-contamination can be effectively removed. A second treatment is performed subsequently to the first treatment in order to remove heavy metals.

The heavy metals may include at least one selected from the group consisting of copper (Cu), zinc (Zn), cadmium (Cd), lead (Pb), arsenic (As), chromium (Cr) and nickel (Ni).

The washing solution used for the removal of heavy metals includes at least one selected from the group consisting of citric acid, oxalate, $H_2CO_3$ and nitric acid. In consideration of economics and environmental safety, types and amounts of the washing solutions vary, according to types and concentrations of the contaminated heavy metals per 1 Kg of the dredged soil.

Heavy metals in marine deposit soil have various levels of toxicity and concentrations and each heavy metal can be divided into three concentration groups—low, medium and high concentrations. It is effective to distinguish types, concentrations and treatment methods according thereto.

TABLE 1

| Conc. | Cu | Zn | Cd | Pb | Cr | Ni | As |
|---|---|---|---|---|---|---|---|
| Low | Less than or equal to 300 | Less than or equal to 500 | Less than or equal to 50 | Less than or equal to 150 | Less than or equal to 100 | Less than 100 | Less than 50 |
| Medium | Greater than 300 but less than 1,000 | Greater than 500 but less than 1,500 | Greater than 50 but less than or equal to 100 | Greater than 150 but less than or equal to 300 | Greater than 100 but less than 300 | Greater than or equal to 100 but less than 200 | Greater than or equal to 50 but less than 100 |
| High | Greater than or equal to 1,000 | Greater than or equal to 1,500 | Greater than 100 | Greater than 300 | Greater than or equal to 300 | Greater than or equal to 200 | Greater than or equal to 100 |

Conc unit: mg/Kg

In regard to ingredients of the washing solution, citric acid may have a concentration of 5 mM to 100 mM, oxalate may have a concentration of 5 mM to 100 mM, EDTA may have a concentration of 10 mM to 50 mM, $H_2CO_3$ may have a concentration of 0.05 M to 0.5 M and nitric acid may have a concentration of 0.05 M to 2 M. The types and concentrations of the washing solution may be as follows according to a degree of contamination of the marine deposit soil.

When concentrations of contaminants are different, a highest concentration becomes a standard.

In the case of low concentration contamination, it is preferable that at least one ingredient selected from the group consisting of citric acid, oxalate, EDTA and $H_2CO_3$ be used, where the concentration of citric acid is 5 mM to 100 mM, that of oxalate is 5 mM to 100 mM, that of EDTA is 10 mM to 50 mM and that of $H_2CO_3$ is 0.05 mM to 0.5 M. In the case of low concentration contamination, it is preferable that citric acid and $H_2CO_3$ are mixed and used. However, when a high concentration contaminant is included among the low concentration contaminants, it is preferable that oxalate be mixed and used. When an EDTA is further mixed, treatment efficiency can greatly increase.

In the case of medium concentration contamination, it is preferable that the first treatment be performed as the low concentration contamination, followed by the second treatment with 0.1 M to 0.5 M of nitric acid. More preferably, citric acid may be mixed and used.

Further, in the case of high concentration contamination, it is preferable that washing be performed using 0.5 M to 2 M, preferably 0.5 M to 1.5 M nitric acid. More preferably, washing with EDTA may be further performed after washing with nitric acid. 50 mM EDTA may be used. Meanwhile, it is preferable that the washing process with nitric acid be performed two to four times.

The washing is performed one to three times at each concentration range and may be performed for 15 minutes to 60 minutes, but is not limited thereto.

Meanwhile, it is preferably that an amount of the washing solution be 21 to 51 per 1 Kg of the contaminated deposit soil.

According to the present disclosure, many side effects of conventional inorganic acid heavy metal eluants in a soil environment can be resolved by minimizing use of generally used inorganic acids and combining with various organic acids.

When the various organic acids are used as a heavy metal eluant and further, when organic acid washing solutions are used with EDTA as in the present disclosure, a problem of soil gap reduction, which is a disadvantage of the organic acids, can be resolved. Additionally, by classifying the washing solutions according to contamination concentrations to use, environmental damages can be significantly reduced and heavy metal contamination can be economically treated.

Further, according to an aspect of the present disclosure, deposit soil including purified deposit soil treated according to the deposit soil treatment method described above is provided, and upon purification, the contaminated deposit soil can be used as reclamation soil.

The purified deposit soil may be included in an amount of 50 wt % to 90 wt %, preferably 70 wt % to 90 wt %, more preferably about 70 wt %, based on a total weight of reclamation soil.

Further, the deposit soil purified according to the present disclosure as described above may be applied to various other construction-related materials, for example, cement substitutes, aggregate, clay blocks, and the like.

The purified deposit soil obtained by the present disclosure is preferably mixed with at least one of sand, sludge impregnated with filamentous fungi, microorganisms and various aggregate such as porous ceramic aggregate, in order to provide soil suitable for the reclamation soil.

More specifically, the reclamation soil of the present disclosure comprises the purified deposit soil treated by the method for treating contaminated soil previously described and an additional ingredient. The purified deposit soil is contained in an amount of 50 wt % to 90 wt %, based on the total weight of the reclamation soil, and the additional ingredient may be included in an amount of 10 wt % to 50 wt %, based on the total weight of the reclamation soil.

The additional ingredient may be one selected from the group consisting of sand, microbial sewage sludge and porous ceramic aggregate.

The porous ceramic aggregate may be, for example, a porous ceramic made with power plant waste recycling technology.

It is preferable that the sludge be sludge impregnated with filamentous fungi, for example, may be one obtained by adding 100 mL/Kg mineral salt medium (MSM) to sewage sludge and mixing, followed by shaking, cultured in an incubator at 28±2° C. for 3 days to 10 days. It is preferable that shaking culture involve stirring; for example, shaking culture may be performed at 100 rpm to 200 rpm for a week.

The reclamation soil made using the purified deposit soil of the present disclosure may be prepared by, for example, mixing 2 parts by weight of one ingredient selected from the group consisting of sand, aggregate, sludge and a microorganism with 8 parts by weight of the purified deposit soil or mixing 2 parts by weight of each of two ingredients selected from the group consisting of sand, aggregate, sludge and a microorganism with 8 parts by weight of the purified deposit soil; for example, mixing the purified deposit soil, sand and sludge or the purified deposit soil, aggregate and sludge at a weight ratio of 8:2:2, respectively.

It is preferable that the reclamation soil mixed as the above be fermented under facultative anaerobic conditions at 28° C. for 1 week to 2 weeks. During this fermentation, filamentous fungi are further impregnated and act as the rebar of reinforced concrete, thereby making the deposit soil more compact.

As previously described, the contamination of deposit soil mostly treated to be discharged offshore can be reduced by simple and economical processes according to the present disclosure, and such purified deposit soil may be variously recycled, for example, as construction aggregate.

Hereinafter, the present disclosure will be described in more detail with reference to the exemplary embodiments. The following embodiments are provided to help in gaining an understanding of the present disclosure and the scope of the present disclosure is not limited thereto.

MODE FOR INVENTION

Examples

1. Establishment of Mixed Strain for Purification of Multi-Contamination
(1) Oil-Decomposing Strain
1) Selection of BTEX-Decomposing Strain
1) Selection Process For BTEX (B: benzene, T: toluene, E: ethylbenzene, X: xylene)-decomposing strains, strains having no impact on strain growth and oil controllability when mixed were selected among those capable of removing oil contamination. A benzene-removing strain *Pseudomonas* sp. BJ10 (100%), a toluene-removing strain *Pseudomonas* sp. T18 (98.7%) and an ethylbenzene-removing strain *Pseudomonas* sp.E41 (99.9%) were mixed to develop a mixed strain which can be used for multi-contamination.

2) Result of BTEX-Contamination Purification

Contamination-free samples were contaminated with low concentration (273.4 mg/Kg), medium concentration (2168.6 mg/Kg) and high concentration (3449.0 mg/Kg) of BTEX. Removal efficiency was measured and the result thereof is shown in Table 2 below.

The low concentration contamination (273.4 mg/Kg) was not detected within 24 hours, that is, was almost purified. For the medium concentration contamination (2168.6 mg/Kg), 330.7 mg/Kg remained after 3 days, indicating that 84.8% was removed, and the contamination was not detected after 7 days. For the high concentration contamination (3449.0 mg/Kg), removal efficiency of 99.3% was exhibited after 3 days.

TABLE 2

Result of BTEX removal efficiency (unit: mg/Kg)

|  |  | Day 0 | Day 1 | Day 3 | R.E. (%) |
|---|---|---|---|---|---|
| Benzene | Low conc. | 14.4 | ND | ND | 100.0 |
|  | Medium conc. | 475.8 | 37.4 | 30.0 | 93.7 |
|  | High conc. | 357.8 | 90.4 | 25.7 | 92.8 |
| Toluene | Low conc. | 87.1 | ND | ND | 100.0 |
|  | Medium conc. | 556.2 | 193.6 | 91.8 | 83.5 |
|  | High conc. | 845.1 | 181.9 | ND | 100.0 |
| Ethyl-benzene | Low conc. | 88.7 | ND | ND | 100.0 |
|  | Medium conc. | 567.7 | 218.0 | 96.8 | 83.0 |
|  | High conc. | 986.7 | 191.0 | ND | 100.0 |
| Xylene | Low conc. | 83.2 | ND | ND | 100.0 |
|  | Medium conc. | 568.9 | 290.0 | 111.6 | 80.4 |
|  | High conc. | 1259.4 | 218.9 | ND | 100.0 |
| BTEX | Low conc. | 273.4 | ND | ND | 100.0 |
|  | Medium conc. | 2168.6 | 698.0 | 330.7 | 84.8 |
|  | High conc. | 3449.0 | 622.2 | 25.7 | 99.3 |

2) Selection of TPH-Decomposing Strain
1) Selection Process

For TPH-decomposing strains, strains having no impact on strain growth and oil controllability when mixed were selected from among those capable of removing oil contamination. To select TPH-decomposing strains, TPH was inoculated as a carbon source in an MSM. Strains with high TPH-decomposition efficiency were selected through screening. By analyzing and measuring with GC-FID, a diesel-removing strain *Pseudomonas* sp. DJ19 (94.8%) was selected.

2) Result of TPH-Contamination Purification 1,000 mg/Kg, 5,000 mg/Kg and 10,000 mg/Kg of TPH were inoculated in contamination-free samples. Removal efficiency thereof was measured and the result thereof is shown in Table 3 below.

TABLE 3

Result of TPH removal efficiency (unit: mg/Kg)

| TPH conc. (mg/Kg) | | Day 0 | Day 1 | Day 3 | Day 7 | R.E. (%) |
|---|---|---|---|---|---|---|
| Low conc. 1000 | Inoculated | 700.4 | 141.5 | 68.1 | N.D. | 100 |
| | soil | 588.9 | 246.4 | 25.9 | N.D. | 100 |
| | Average | 644.7 | 193.9 | 47.0 | N.D. | 100 |
| | (STD) | (55.8) | (52.5) | (21.1) | | |
| Medium conc. 5000 | Inoculated | 6389.3 | 1550.2 | 936.9 | 53.1 | 99.2 |
| | soil | 4899.2 | 2608.7 | 714.2 | 209.6 | 95.7 |
| | Average | 5644.2 | 2079.4 | 825.5 | 131.4 | 97.7 |
| | (STD) | (745.0) | (529.3) | (111.4) | (78.2) | |
| High conc. 10000 | Inoculated | 9449.9 | 3075.3 | 1715.6 | 354.2 | 96.3 |
| | soil | 8118.5 | 1313.4 | 639.2 | 165.5 | 98.0 |
| | Average | 8784.2 | 2194.3 | 1177.4 | 259.9 | 97.0 |
| | (STD) | (665.7) | (880.9) | (538.2) | (94.3) | |

The concentrations were measured twice and averages and deviations thereof are also indicated in Table 3 above.

It was confirmed that the TPH artificial contamination was not detected (N.D) at its concentration of 1,000 mg/Kg 7 days after strain inoculation, and when the concentrations thereof were 5,000 mg/Kg and 10,000 mg/Kg, the removal efficiencies were 97.7% and 97.0%, respectively, 7 days after strain inoculation.

3) Selection of PAH-Decomposing Strain

1) Selection Process

For PAH-decomposing strains, strains having no impact on strain growth and oil controllability when mixed were selected from among those capable of removing aromatic compounds.

A mineral basal salt (MBS) solid medium was used to select PAH-decomposing strains, and the solid medium was coated with the PAH on a surface thereof. A colony grown in the PAH-coated medium was first purely isolated, and PAH removal efficiency was measured using the isolated strain. The result was analyzed and measured using gas chromatography with a flame-ionization detector (GC-FID). PAH-removing *Rhodococcus* sp. PHEN3 (86.5%) was selected.

2) Result of PAH-Contamination Purification

A sample was obtained from Dongbin Inner Harbor, Pohang, South Korea, and a calibration curve was prepared using 5 PAH materials including phenanthrene, anthracene, fluoranthene, pyrene, benzo[a]pyrene. The PAH removal efficiency was measured using the selected *Rhodococcus* sp. PHEN3, and the result thereof is shown in Table 4 below.

TABLE 4

Result of PAH removal efficiency observation (unit: mg/Kg)

| | Dongbin Inner Harbor, Pohang, South Korea | | | |
|---|---|---|---|---|
| PAH | Day 0 | Day 1 | Day 3 | R.E. (%) |
| Phenanthrene | 0.50 | 0.29 | 0.22 | 56.9 |
| Anthracene | 0.58 | 0.35 | 0.05 | 90.8 |

TABLE 4-continued

Result of PAH removal efficiency observation (unit: mg/Kg)

| | Dongbin Inner Harbor, Pohang, South Korea | | | |
|---|---|---|---|---|
| PAH | Day 0 | Day 1 | Day 3 | R.E. (%) |
| Fluoranthene | 3.21 | 1.93 | 0.65 | 79.7 |
| Pyrene | 8.70 | 4.27 | 0.28 | 96.8 |
| Benzo[a]pyrene | 4.16 | 2.30 | 0.32 | 92.3 |
| Total | 17.14 | 9.15 | 1.50 | 91.1 |

When the *Rhodococcus* sp. PHEN3 was applied to the samples of Dongbin Inner Harbor, Pohang, the average of 17.14 mg/Kg was reduced to 1.50 mg/Kg after 3 days, indicating removal efficiency of 91.2%.

(2) Marine Nutritive Salt-Decomposing Strain

1) Selection Process

For marine nutritive salt (total nitrogen/total phosphorous: TN/TP)-decomposing strains, strains having no impact on strain growth and inorganic nutritive salt controllability when mixed were selected from among those capable of removing TN/TP. Sea water was collected from the southern coast of Korea to select marine nutritive salt (TN/TP)-decomposing strains, and marine microorganisms were purely isolated using an R2A medium. To select ammonia nitrogen-controlling strains, the purely isolated strains were inoculated in a modified MSM (Mineral Salt Medium) and ammonia nitrogen removal efficiency was measured. To select phosphorous-controlling strains, the purely isolated strains were inoculated in a marine broth followed by measuring removal efficiency. As a result, a TN-removing strain *Achromobacter* sp. A-1 and a TP-removing strain *Pseudomonas* sp. 2J were selected.

2) Result of Marine Nutritive Salt (TN/TP)-Contamination Purification

A TN/TP contamination purification experiment was carried out using samples having a high concentration of contaminants (TN: 120 ppm, TP: 20 ppm) from Dadaepo Harbor. As a result of the TN removal efficiency experiment using the Dadaepo Harbor samples, the efficiency of *Achromobacter* sp. A-1 was 78.91%, as shown in Table 5 below. Using the same samples from Dadaepo Harbor, TP removal efficiency experiment was carried out, and as a result, the efficiency of *Pseudomonas* sp. 2J of 79.41% was measured.

TABLE 5

Result of TN/TP removal efficiency using samples from Dadaepo Harbor (unit; mg/Kg)

| Strains | | Day 0 | Day 1 | Day 3 | Day 7 | R.E. (%) |
|---|---|---|---|---|---|---|
| Achromobacter A-1 | TN conc. | 20.50 | 15.00 | 11.00 | 4.10 | |
| | | 25.50 | 14.70 | 14.00 | 5.60 | |
| | Average | 23.00 | 14.85 | 12.50 | 4.85 | 78.91 |
| | (STD.) | (3.54) | (0.21) | (2.12) | (1.06) | |
| Pseudomonas 2J | TP conc. | 5.00 | 4.30 | 3.60 | 0.90 | |
| | | 5.20 | 3.90 | 2.80 | 1.20 | |
| | Average | 5.10 | 4.10 | 3.20 | 1.05 | 79.41 |
| | (STD.) | (0.14) | (0.28) | (0.57) | (0.21) | |

The concentrations were measured twice and averages and deviations thereof are also indicated in Table 5 above.

(3) TCE-Decomposing Strain

1) Selection Process

For TCE-decomposing strains, strains having no impact on strain growth and TCE controllability when mixed were selected among those capable of removing TCE compounds. An MSM (Mineral Salt Medium) was used to select TCE-decomposing strains, while TCE was inoculated as a carbon source. Strains decomposing TCE in high efficiency were selected through screening and analyzed and measured using GC-FID to select *Pseudomonas* sp. UI2 (98.0%).

2) Result of TCE Contamination Purification

In order to evaluate TCE removal efficiency, each sample was inoculated with 1 mg/Kg, 5 mg/Kg and 10 mg/Kg of TCE in contamination-free samples, and a TCE-removing strain was inoculated in an experimental group. The result thereof is shown in Table 6 below.

TABLE 6

Result of TCE removal efficiency (unit: mg/Kg)

| TCE conc. (mg/Kg) | | Day 0 | Day 1 | Day 3 | R.E. (%) |
|---|---|---|---|---|---|
| 1 | Inoculated soil | 1.9 | 1.1 | 0.4 | 79.0 |
|   |   |   | 0.9 | 0.2 | 89.5 |
|   | Average(STD) | 1.9 | 1.0 (0.1) | 0.3 (0.1) | 84.2 |
| 5 | Inoculated soil | 6.4 | 2.2 | 2.0 | 68.7 |
|   |   |   | 3.2 | 2.0 | 69.4 |
|   | Average(STD) | 6.4 | 2.7 (0.5) | 2.0 (0.0) | 69.1 |
| 10 | Inoculated soil | 9.7 | 3.4 | 2.6 | 73.4 |
|   |   |   | 5.0 | 2.2 | 77.3 |
|   | Average(STD) | 9.7 | 4.2 (0.8) | 2.4 (0.2) | 75.4 |

The concentrations were measured twice and averages and deviations thereof are also indicated in Table 6 above.

(4) Establishment of Mixed Strain

1) Mixed Strain of the Present Disclosure

A mixed strain was established by mixing the strains selected in 1) to 3), and was deposited in the National Institute of Agricultural Sciences as NIX51 under Deposition No. KACC81038BP on Dec. 22, 2016, and obtained Accession No. KACC81038BP.

2. Establishment of Multi-Contamination Purification Process (1) Preparation of Artificial Multi-Contamination Soil Sample The following contaminants were mixed in the indicated concentrations in order to prepare artificial multi-contamination soil of marine deposit soil.

BTEX concentration: 2,000 mg/Kg, -TPH: 5,000 mg/Kg, -PAH: 30 mg/Kg

Concentration of marine nutritive salts (TN): 50 mg/Kg, -TP: 10 mg/Kg.

TCE concentration: 10 mg/Kg

Concentration of heavy metal contamination: copper (1500 mg/Kg), zinc (2000 mg/Kg), cadmium (200 mg/Kg), lead (600 mg/Kg), chrome (400 mg/Kg), nickel (200 mg/Kg), arsenic (100 mg/Kg)

(2) Observation of Effect of Mixed Strain of the Present Disclosure on Dredged Soil Purification 1 g/L of the mixed strain of the present disclosure was inoculated in the marine deposit soil artificially contaminated to have such ingredients, and samples were collected at day 0, day 7 and day 14, and analyzed and measured using GC-FID. The result is shown in Table 7 below.

TABLE 7

Result of contaminated dredged soil purification (unit: mg/Kg)

| Contam-inants | | Day 0 | Day 1 | Day 3 | Day 7 | Removal rate (%) |
|---|---|---|---|---|---|---|
| BTEX | Benzene | 293.8 | ND | ND | ND | 100 |
|   | Toluene | 477.3 | 87.7 | ND | ND | 100 |
|   | Ethylbenzene | 513.8 | 90.0 | 85.2 | ND | 100 |
|   | Xylene | 539.2 | 66.6 | ND | ND | 100 |
|   | BTEX | 1824.1 | 254.3 | 85.2 | ND | 100 |
| TPH |   | 5,076 | 1583.5 (101.1) | 871.7940 .2) | 297.9 (57.1) | 94.1 |
| PAH | Phenanthrene | 20.08 | 10.86 | 5.61 | 4.95 | 75.33 |
|   | Anthracene | 9.18 | 1.67 | 1.40 | 1.81 | 80.28 |
|   | Fluoranthene | 8.25 | 4.37 | 1.83 | 1.33 | 83.84 |
|   | Pyrene | 4.18 | 2.81 | 1.06 | 0.86 | 79.51 |
|   | Benzo[a]pyrene | 9.56 | 3.60 | 1.30 | 0.87 | 90.86 |
|   | PAH | 51.26 | 25.33 (4.50) | 11.52 (0.77) | 9.83 (3.02) | 80.83 |
| TCE |   | 10.2 | 5.1 (0.5) | ND | ND | 100 |
| TN |   | 31.5 | 27.0 | 23.0 | 35.51 |   |
| TP |   | 10.60 | 2.48 (0.54) | 2.95 (0.35) | 64.90 |   |

As shown in Table 7 above, it can be understood from the result that highly volatile contaminants are rapidly removed during periodic mixing along with microbial actions, and purified to a level where they are not detectable after 3 days, and the remaining contaminants are also purified to a level below legal limits without affecting each other when mixed as the result of single contamination. It is also seen that those contaminants not purified for 7 days were all purified within 14 days.

3. Establishment of Heavy Metal Purification Process

Marine soil was artificially contaminated with low, medium and high concentrations of heavy metals as shown in Table 8 below.

TABLE 8

|   | Cu | Zn | Cd | Pb | Cr | Ni | As |
|---|---|---|---|---|---|---|---|
| Low | 300 | 500 | 50 | 150 | 100 | 50 | 25 |
| Medium | 700 | 1,000 | 100 | 300 | 200 | 100 | 50 |
| High | 1,500 | 2,000 | 200 | 600 | 400 | 200 | 100 |

In the case of multi-contamination, contamination concentrations of the heavy metals were as follows:

Copper (1500 mg/Kg), zinc (2000 mg/Kg), cadmium (200 mg/Kg), lead (600 mg/Kg), chrome (400 mg/Kg), nickel (200 mg/Kg) and arsenic (100 mg/Kg).

For the low concentration contamination, 50 mM of citric acid and 0.1 M of $H_2CO_3$ were used as the eluant. For the medium concentration, 50 mM of citric acid and 0.1 M of nitric acid were used while 1 M of nitric acid was used as the eluant for the high concentration. Concentrations of the heavy metals left after the eluant treatment are shown in Table 9 below.

TABLE 9

Result of heavy metal single contamination purification

|   |   | Cu | Zn | Cd | Pb | Cr | Ni | As |
|---|---|---|---|---|---|---|---|---|
| Low conc. | Pre-treatment | 300 | 500 | 50 | 150 | 100 | 50 | 25 |
|   | Post-treatment | 33.5 | 79.6 | 3.2 | 73.3 | 43.6 | 18.7 | — |
|   | R.E. (%) | 88.8 | 84.1 | 93.6 | 51.1 | 56.4 | 62.6 | — |

TABLE 9-continued

Result of heavy metal single contamination purification

|  |  | Cu | Zn | Cd | Pb | Cr | Ni | As |
|---|---|---|---|---|---|---|---|---|
| Medium conc. | Pre-treatment | 700 | 1000 | 100 | 300 | 200 | 100 | 50 |
|  | Post-treatment | 12.3 | 61.2 | 0.1 | 20.9 | 60.6 | 20.7 | — |
|  | R.E. (%) | 98.2 | 93.9 | 99.9 | 93.0 | 69.7 | 79.3 | — |
| High conc. | Pre-treatment | 1500 | 2000 | 200 | 600 | 400 | 200 | 100 |
|  | Post-treatment | 15.2 | 88.1 | 0.1 | 35.6 | 60.9 | 22.1 | — |
|  | R.E. (%) | 99.0 | 95.6 | 100.0 | 94.1 | 84.8 | 89.0 | — |

*Analysis Institution: Marine Environment Management Corporation

Further, a purification experiment was performed on heavy metal multi-contamination as shown in Table 10 below. 1 M nitric acid was used as the eluant to purify the contamination.

TABLE 10

Result of heavy metal multi-contamination purification

|  |  | Cu | Zn | Cd | Pb | Cr | Ni | As |
|---|---|---|---|---|---|---|---|---|
| Multi-contamination | Pre-treatment | 1500 | 2000 | 200 | 600 | 400 | 200 | 100 |
|  | Post-treatment | 31.7 | 32.5 | 0.2 | 10.8 | 34.1 | 10.5 | — |
|  | R.E. (%) | 97.9 | 98.4 | 99.9 | 98.2 | 91.5 | 94.8 | — |

*Analysis Institution: Marine Environment Management Corporation

When purifying the heavy metals, environmental toxicity was minimized, and in consideration of economics, a number of washing solutions used varied according to types and concentrations of the contaminated heavy metals, and so did the treatment methods. Both single contamination and multi-contamination involve purification below legal limits. Although high concentration contamination does not frequently occur in Korea, a possibility of high concentration contamination purification was measured in consideration of the technology entering overseas markets in the future.

4. Recycling of Purified Deposit Soil

Currently, dredged sand generated by port development and operation in Korea is mostly disposed in coastal landfills, and some is disposed in the ocean. A recycling rate of marine dredging pails generated in Korea is about 10%, whereas 55% of dredged soil is recycled in Europe. Accordingly, there is an urgent need for the dredged soil treatment to develop uses for contaminant purification and recycling.

(1) Preparation of Reclamation Soil Using Purified Deposit Soil

In order to use the purified deposit soil as dredged soil, properties of the purified deposit soil should be adjusted to landfill conditions. In terms of the establishment of a heavy metal purification process of 3, reclamation soil was manufactured using the purified deposit soil obtained as a result of the heavy metal multi-contamination purification was manufactured in this experiment.

2 parts by weight of each of the additional ingredients 1 to 4, 7 and 8 of Table 11 below was additionally added to 8 parts by weight of the deposit soil and mixed to measure changes in deposit soil properties.

The sludge in Table 11 below is obtained from a sewage disposal plant. 100 mL/Kg of an MSM inorganic medium was added to the sludge of the sewage disposal plant, inserted into an incubator and shaking cultured at 28±2° C. for 7 days at 100 rpm to 200 rpm. The total microorganisms and filamentous fungi were impregnated in the sludge.

The aggregate in Table 11 is made with a porous ceramic made using power plant waste recycling technology.

TABLE 11

| No. 1 | No. 2 | No. 3 | No. 4 | No. 7 | No. 8 |
|---|---|---|---|---|---|
| Sand | Sand/Sludge | Aggregate | Aggregate/Sludge | Sludge | Microorganism |

In sample Nos. 2 and 4, the additional ingredients, in which 2 ingredients are mixed at the same weight ratio, were used. More specifically, for sample Nos. 1, 3, 7 and 8, 2 parts by weight of each of the sand, aggregate, sludge and microorganisms were mixed with 8 parts by weight of the purified deposit soil. In the case of sample No. 2, the purified deposit soil, sand and sludge were mixed at a weight ratio of 8:2:2 while the purified deposit soil, aggregate and sludge were mixed at a weight ratio of 8:2:2 in sample No. 4.

Consequently, the experiment result was analyzed by Korea Research Institute for Construction Testing, and the result thereof is shown in Table 12 and FIGS. 1 to 7. Purified marine deposit soil to which no additional ingredients were added was used as a control.

TABLE 12

Result of analysis of purified marine deposit soil properties

| Sample No. | Natural moisture % | Soil density g/cm3 | Liquid limit % | Plastic limit % | Plastic index — | Max particle diameter mm | 5 mm Sieve passing % | 0.8 mm Sieve passing % | Classification of soil — |
|---|---|---|---|---|---|---|---|---|---|
| No. 1 | 50.3 | 2.677 | 50.5 | 26.7 | 23.8 | 4.75 | 100 | 59.8 | CH |
| No. 2 | 48.9 | 2.685 | 47.9 | 25.2 | 22.7 | 4.75 | 100 | 56.9 | CL |
| No. 3 | 64.4 | 2.658 | 57.8 | 27.2 | 30.6 | 9.5 | 78 | 57.5 | CH |
| No. 4 | 60.1 | 2.653 | 56.8 | 27.6 | 29.2 | 9.5 | 82 | 66.1 | CH |
| No. 7 | 68.0 | 2.656 | 57.5 | 25.9 | 31.6 | 4.75 | 100 | 93.5 | CH |
| No. 8 | 70.9 | 2.653 | 55.1 | 26.9 | 28.2 | 4.75 | 100 | 94.8 | CH |
| Control | 110.5 | 2.600 | 54.7 | 28.3 | 26.4 | 0.85 | 100 | 98.7 | CH |

As confirmed in Table 12 and FIGS. 1 to 7, sample No. 2 is the most preferable to be used as reclamation soil.

While embodiments have been shown and described in detail above, it will be apparent to those skilled in the art that modifications and variations could be made without departing from the scope of the present disclosure as defined by the appended claims.

Depositary Institute: National Institute of Agricultural Sciences

Accession No.: KACC81038BP

Date of deposit: Dec. 22, 2016

The invention claimed is:

1. A method for treating contaminated deposit soil, the method comprising:
   a first treatment involving inoculating a mixed strain NIX51 (KACC81038BP), which consists of *Pseudomonas* sp. BJ10, *Pseudomonas* sp. T18, *Pseudomonas* sp. E41, *Pseudomonas* sp. DJ19, *Rhodococcus* sp. PHEN3, *Achromobacter* sp. A-1, *Pseudomonas* sp. 2J and *Pseudomonas* sp. UI2, in the contaminated deposit soil to treat an organic contaminant in a bioreactor; and
   a second treatment involving washing the treated deposit soil with a washing solution comprising at least one selected from the group consisting of citric acid, oxalate, carbonic acid ($H_2CO_3$) and nitric acid to dispose of a heavy metal,
   wherein the organic contaminant is at least one multi-contamination selected from the group consisting of oil, total petroleum hydrocarbons (TPH), polycyclic aromatic hydrocarbon (PAH), nutritive salts, and trichloroethylene (TCE).

2. The method for treating contaminated deposit soil of claim 1, wherein the oil comprises: benzene, toluene, ethylbenzene and xylene.

3. The method for treating contaminated deposit soil of claim 1, wherein the mixed strain is inoculated in an amount of 0.1 g to 2 g by wet weight of a mixed strain per 1 Kg of the deposit soil.

4. The method for treating contaminated deposit soil of claim 1, wherein the first treatment is carried out at 10° C. to 35° C. at pH 6.5 to pH 7.5 under aerobic conditions for 3 days to 14 days.

5. The method for treating contaminated deposit soil of claim 1, wherein the heavy metal comprises at least one selected from the group consisting of copper (Cu), zinc (Zn), cadmium (Cd), lead (Pb), arsenic (As), chromium (Cr) and nickel (Ni).

6. The method for treating contaminated deposit soil of claim 1, wherein, in the second treatment, the washing solution comprises at least one component selected from the group consisting of citric acid, oxalate, and carbonic acid when the heavy metal is at a low concentration based on Table 1:

TABLE 1

| Conc. | Cu | Zn | Cd | Pb | Cr | Ni | As |
|---|---|---|---|---|---|---|---|
| Low | 300≥ | 500≥ | 50≥ | 150≥ | 100≥ | 100> | 50> |
| Medium | 300<- <1,000 | 500<- <1,500 | 50<- ≤100 | 150<- ≤300 | 100<- <300 | 100≤- <200 | 50≤- <100 |
| High | 1,000≤ | 1,500≤ | 100< | 300< | 300≤ | 200≤ | 100≤ | concentration unit: mg/Kg.

7. The method for treating contaminated deposit soil of claim 6, wherein the citric acid, oxalate and $H_2CO_3$ are comprised at concentrations of 5 mM to 100 mM, 5 mM to 100 mM and 0.05 mM to 0.5 mM, respectively, in the washing solution.

8. The method for treating contaminated deposit soil of claim 1, wherein, in the second treatment, the washing solution comprises the nitric acid at a concentration of greater than or equal to 0.1 M and less than 0.5 M when the heavy metal is at a medium concentration based on Table 1:

TABLE 1

| Conc. | Cu | Zn | Cd | Pb | Cr | Ni | As |
|---|---|---|---|---|---|---|---|
| Low | 300≥ | 500≥ | 50≥ | 150≥ | 100≥ | 100> | 50> |
| Medium | 300<- <1,000 | 500<- <1,500 | 50<- ≤100 | 150<- ≤300 | 100<- <300 | 100≤- <200 | 50≤- <100 |
| High | 1,000≤ | 1,500≤ | 100< | 300< | 300≤ | 200≤ | 100≤ | concentration unit: mg/Kg.

9. The method for treating contaminated deposit soil of claim 1, wherein, in the second treatment, the washing solution comprises the nitric acid at a concentration of 0.5 M to 1 M when the heavy metal is at a high concentration based on Table 1:

TABLE 1

| Conc. | Cu | Zn | Cd | Pb | Cr | Ni | As |
|---|---|---|---|---|---|---|---|
| Low | 300≥ | 500≥ | 50≥ | 150≥ | 100≥ | 100> | 50> |
| Medium | 300<- <1,000 | 500<- <1,500 | 50<- ≤100 | 150<- ≤300 | 100<- <300 | 100≤- <200 | 50≤- <100 |
| High | 1,000≤ | 1,500≤ | 100< | 300< | 300≤ | 200≤ | 100≤ | concentration unit: mg/Kg.

* * * * *